US00PP32589P3

(12) United States Plant Patent
Biancheri

(10) Patent No.: US PP32,589 P3
(45) Date of Patent: Dec. 8, 2020

(54) ***RANUNCULUS* PLANT NAMED 'ABPEGASO'**

(50) Latin Name: *Ranunculus asiaticus*
Varietal Denomination: ABPEGASO

(71) Applicant: Impresa Individuale Biancheri Alberto, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 16/873,432

(22) Filed: Apr. 10, 2020

(65) Prior Publication Data

US 2020/0352073 P1 Nov. 5, 2020

(30) Foreign Application Priority Data

May 2, 2019 (QZ) ..... PBR 2019/1131

(51) Int. Cl.
*A01H 6/72* (2018.01)
*A01H 5/02* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72
See application file for complete search history.

*Primary Examiner* — Annette H Para
(74) *Attorney, Agent, or Firm* — Cassandra Bright

(57) ABSTRACT

A new and distinct cultivar of *Ranunculus* plant named 'ABPEGASO' is disclosed, characterized by plants producing a large number of very large light pink flowers with a typical vase life of 20 to 25 days. Plants have a unique foliage carriage, with foliage occurring at the base of the plant. The new variety is a *Ranunculus*, normally produced as a cut flower and potentially useful as an ornamental plant.

1 Drawing Sheet

Latin name of the genus and species: *Ranunculus asiaticus*.

Variety denomination: 'ABPEGASO'.

BACKGROUND OF THE INVENTION

The new *Ranunculus* cultivar is a product of a planned breeding program conducted by the inventor, Alberto Biancheri at a research nursery in Camporosso Mare, Italy. The cross resulting in this new variety was made during 2013.

The seed parent is the, unpatented, variety of *Ranunculus* 'ABROCHI'. The pollen parent is the unpatented, proprietary variety referred to as *Ranunculus* '131-07/A'. The new variety was discovered in 2015 by the inventor in a group of seedlings resulting from the 2013 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2015 and has shown that the unique features of this cultivar are stable and reproduced true to type in multiple successive generations.

SUMMARY OF THE INVENTION

The cultivar 'ABPEGASO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABPEGASO' These characteristics in combination distinguish 'ABPEGASO' as a new and distinct *Ranunculus* cultivar:

1. Very large light pink flowers.
2. High quantity of flowers produced per plant.
3. Low foliage carriage, flowers occurring high above a low growing plant.
4. Long vase life.
5. Flower diameter of 12 to 14 cm.

PARENT COMPARISON

Plants of the new cultivar 'ABPEGASO' are similar to plants of the seed parent, in most horticultural characteristics, however, plants of the new cultivar 'ABPEGASO' differ in the following;

1. Flowers of the new variety are light pink, those of the seed parent are pale salmon.
2. Vegetative carriage of the new variety is lower than that of the seed parent.

Plants of the new cultivar 'ABPEGASO' are similar to plants of the pollen parent, in most horticultural characteristics, however, plants of the new cultivar 'ABPEGASO' differ in the following;

1. Flowers of the new variety are a different color than those of the pollen parent.
2. Flowers of the new variety are larger than flowers of the pollen parent.

COMMERCIAL COMPARISON

Plants of the new cultivar 'ABPEGASO' are comparable to the commercial variety *Ranunculus* 'ABSIRLPIN', U.S.

Plant Pat. No. 30,388. The two *Ranunculus* varieties are similar in most horticultural characteristics; however, the new variety 'ABPEGASO' differs in the following:

1. This comparator produces more foliage.
2. Flowers of the new variety are taller, 6 to 7 cm high, while flowers of this comparator are on average 3 to 4.5 cm high.
3. Flower color of the new variety is light pink, flower color of this comparator is more salmon colored.

BRIEF DESCRIPTION OF THE PHOTOGRAPHS

The accompanying photograph illustrates a close-up view of an individual flowers. The flowering plants of the new variety in the photograph are approximately six months old, grown in a greenhouse during April in Camporosso, Italy. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 5-month-old 'ABPEGASO' plants grown in a greenhouse in Camporosso Mare, Italy. The plant has been described in the month of February. In order to protect the crop against pests, some chemical treatments are performed. Treatments with growth regulators can be performed to limit the plant sizes. In particular, no growth regulators have been applied on the plant described. The rhizome has been planted on raised benches in a peat and pumice substrate mixture. The growing temperature ranged from 12° C. to 26° C. during the day and from 0° C. to 6° C. during the night. General light conditions are bright, normal sunlight. Measurements and numerical values represent averages of typical plant types.

Botanical classification: *Ranunculus asiaticus* 'ABPEGASO'.

PROPAGATION

Time to rooting: 15 days at approximately 10-12° C.
Time to produce a rooted plantlet: 20 days.
Root description: Tuberous root.

PLANT

Growth habit: Herbaceous perennial, semi-prostrate vegetation.
Height to top flower: 45 to 50 cm.
Leaf height: 30 to 35 cm.
Plant spread: 40 to 45 cm.
Growth rate: Medium.
Branching characteristics: Main floral stems grow from a basal rosette with 1 or 2 lateral branches, each one of which has one or more flowers.
Length of lateral branches: 40 to 45 cm.
Diameter of lateral branches: 7 to 10 mm.
Texture of lateral branches: Slightly tomentose.
Internode length: Internodes are extremely close together, forming a basal rosette.
Strength of lateral branches: Strong.
Color of lateral branches: Near RHS Yellow-Green 145C.
Aspect/angle of branches: 20° to 30°.
Number of leaves per lateral branch: Usually 2.

FOLIAGE

The plant has a marked heterophylly that means that in the same plant the leaves may have different size and arrangement (simple, ternate and biternate), in relation to the degree of development (young leaf and mature leaf) and their position on the plant (basal leaf—leaf at the base of the plant—and cauline leaf—leaf inserted at the nodes of the floral stems). In other words, there are significant variation in leaf shape on a same plant.

Leaf at the base of the plant:

*Arrangement.*—Simple (young leaf); Ternate (mature leaf).
*Average length.*—20 to 22 cm.
*Average width.*—10 to 15 cm.
*Overall shape of blade.*—Obovate (young leaf); Palmatipartite (mature leaf).
*Dissected leaves, describe lobes, quantity of dissection.*—Young leaves are generally not lobed or a little lobed; mature leaves are generally divided in 3 parts, each one of which is further divided in 3 or more lobes.
*Apex.*—Rounded.
*Base.*—Acute.
*Attachment.*—Petiolate.
*Margin.*—Dentate.
*Texture of top surface.*—Glabrous.
*Texture of bottom surface.*—Glabrous.
*Appearance of top surface.*—Glossy.
*Appearance bottom surface.*—Glossy.
*Leaf internode length.*—The internodes are extremely close together, forming a basal rosette.
*Color.*—Young foliage upper side: RHS Green 137A. Young foliage under side: RHS Yellow-Green 146B. Mature foliage upper side: RHS Green 137B. Mature foliage under side: RHS Yellow-Green 146B.
*Venation.*—Type: Dichotomous; plunging into the limb at the upper surface; raised on the limb at the lower surface. Venation color upper side: RHS Yellow-Green 146B. Venation color under side: RHS Green 137B.
*Petiole.*—Cross section: Round. Length: Average range 11 to 16 cm. Diameter: Average range 0.5 to 1.0 cm. Pubescence: Slightly tomentose. Color: RHS Yellow-Green 145C.

Leaf inserted at the nodes of the floral stems:

*Arrangement.*—Biternate.
*Average length.*—20 to 25 cm.
*Average width.*—15 to 20 cm.
*Overall shape of blade.*—Palmatipartite.
*Dissected leaves, describe lobes, quantity of dissection.*—Generally divided in 3 parts, each one of which is further divided in many lobes.
*Apex.*—Acute.
*Base.*—Attenuate.
*Attachment.*—Petiolate.
*Margin.*—Dentate.
*Texture of top surface.*—Glabrous.
*Texture of bottom surface.*—Glabrous.
*Appearance of top surface.*—Glossy.
*Appearance bottom surface.*—Glossy.

*Leaf internode length*.—Average 10 to 15 cm.

*Color*.—Foliage upper side: RHS Green RHS 137B. Foliage under side: RHS Yellow-Green 146B.

*Venation*.—Type: Dichotomous, plunging into the limb at the upper surface and raised on the limb at the lower surface. Venation color upper side: RHS Yellow-Green 146B. Venation color under side: RHS Green 137B.

*Petiole*.—Cross-section: Round. Length: Average 10 to 15 cm. Diameter: Average 0.5 to 1.0 cm. Pubescence: Slightly tomentose. Color: RHS Yellow-Green 146B.

FLOWER

Quantity per plant: 10 to 12.

Bloom period: Winter to Spring.

Vase life (cut flower): 20 to 25 days.

Persistent or self-cleaning: Self-Cleaning.

Bud:

*Closed bud*.—Shape: Flattened globular with a sharp point. Length: Average 1.5 to 3.0 cm. Diameter: Average 1.0 to 2.5 cm. Color: RHS Yellow-Green 146B.

*Slightly open bud*.—Shape: Flattened globular. Length: Average 2.5 to 3.5 cm. Diameter: Average 2.0 to 2.5 cm. Color: RHS Yellow-Green 145C.

Flower:

*Fully open diameter: Average* 12 to 14 cm.

*Fully open height: Average* 6 to 7 cm.

Corolla: Round, regular, in cross-section.

Petals:

*Arrangement*.—Imbricated, disposed on the receptacle in very tight verticils. The size of the petals is quite variable, according to the position in the corolla, decreasing from the exterior toward the center.

*Average size*.—

*Lobe length*.—Average 6.0 to 6.5 cm.

*Lobe width*.—Average 5.5 to 6.0 cm.

*Quantity*.—Double flower, petals are very numerous (>100).

*Texture*.—Silky, resistant.

*Lobe apex*.—Rounded.

*Lobe shape*.—Obovate.

*Margin*.—Finely Crenate or entire.

*Aspect*.—Concave. Slightly reflexed back when fully open.

*Color when opening*.—Upper surface: Near RHS Red 49D. Lower surface: Near RHS Red 49D.

*Color fully opened*.—Upper surface: Near RHS Red-Purple 65C. Lower surface: Near RHS Red-Purple 65C.

Calyx/sepals:

*Quantity per flower*.—4 or 5.

*Shape*.—Rounded deltate.

*Length*.—Average 2.0 to 4.0 cm.

*Width*.—Average 0.5 to 1.0 cm.

*Apex*.—Acute.

*Base*.—Truncate.

*Margin*.—Entire.

*Texture*.—Lower surface: Glabrous. Upper surface: Glabrous.

*Color*.—Upper Surface: RHS Yellow-Green 146B. Lower Surface: RHS Green 138B.

Peduncle: None.

Pedicel:

*Length*.—Average range 38 to 46 cm.

*Diameter*.—Average range 1.0 to 1.5 cm.

*Color*.—RHS Yellow-Green 144A.

*Orientation*.—Upright.

*Pubescence*.—Slightly tomentose.

Fragrance: None.

REPRODUCTIVE ORGANS

Androecium: Absent.

Gynoecium: The pistils are numerous, short, locked together at the center of the corolla, dome-shaped apocarpous gynoecium.

*Pistil color*.—Near RHS Yellow-Green 144A.

*Nectar glands*.—Absent.

OTHER CHARACTERISTICS

Disease resistance: Not observed.

Drought tolerance and cold tolerance: No differences have been noted in comparison to the common tolerance characteristics to other *Ranunculus* cultivars.

Fruit/seed production: Not observed.

What is claimed is:

1. A new and distinct cultivar of *Ranunculus* named 'ABPEGASO' as herein illustrated and described.

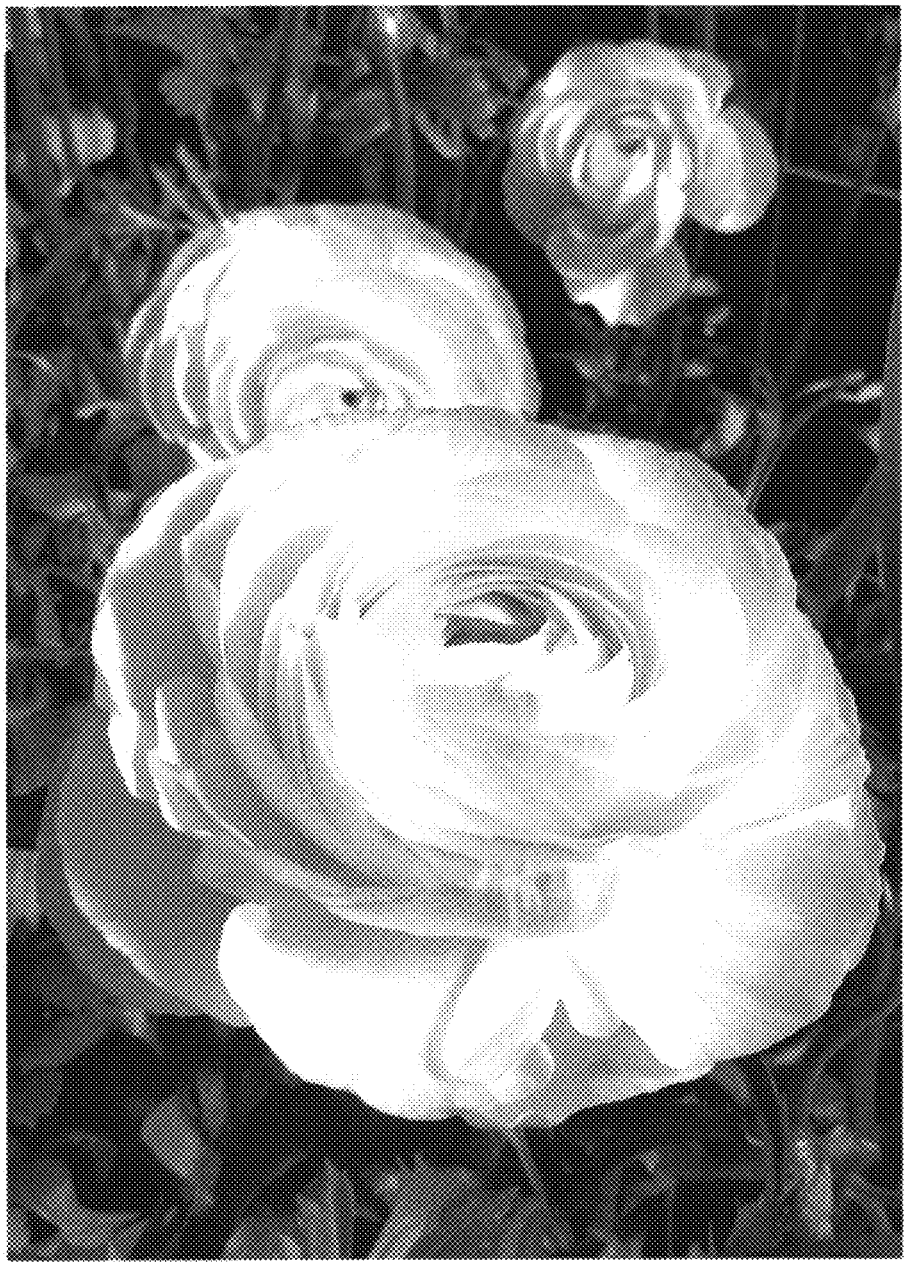

* * * * *